United States Patent [19]

Mason et al.

[11] Patent Number: 5,827,208

[45] Date of Patent: Oct. 27, 1998

[54] HINGE FOR AN ORTHOPEDIC BRACE HAVING A SELECTIVELY POSITIONABLE STOP TO LIMIT ROTATION

[75] Inventors: Bradley R. Mason, Olivenhain; Jeffrey T. Mason, Escondido, both of Calif.

[73] Assignee: Breg, Inc,, Vista, Calif.

[21] Appl. No.: 886,608

[22] Filed: Jul. 1, 1997

Related U.S. Application Data

[63] Continuation-in-part of Ser. No. 563,659, Nov. 28, 1995, Pat. No. 5,672,152.

[51] Int. Cl.⁶ .......................................................... A61E 5/00
[52] U.S. Cl. ................................................ 602/16; 602/26
[58] Field of Search .................................... 602/5, 16, 20, 602/23, 26

[56] References Cited

U.S. PATENT DOCUMENTS

| | | |
|---|---|---|
| 401,933 | 4/1889 | De Camp . |
| 2,812,961 | 11/1957 | Brown et al. ........................ 602/16 X |
| 3,439,672 | 4/1969 | Fisher . |
| 4,463,751 | 8/1984 | Bledsoe ..................................... 602/16 |
| 4,481,941 | 11/1984 | Rolfes . |
| 4,620,532 | 11/1986 | Houswerth . |
| 4,817,588 | 4/1989 | Bledsoe . |
| 4,846,842 | 7/1989 | Connolly et al. ..................... 602/26 X |
| 4,982,732 | 1/1991 | Morris . |
| 5,000,169 | 3/1991 | Swicegood et al. . |
| 5,062,858 | 11/1991 | Broeck et al. ............................. 623/43 |
| 5,292,303 | 3/1994 | Bastyr et al. ............................. 602/16 |
| 5,399,154 | 3/1995 | Kipnis et al. ........................ 602/16 X |
| 5,409,449 | 4/1995 | Nebolon ..................................... 602/16 |
| 5,419,754 | 5/1995 | Hutchins ................................... 602/16 |
| 5,443,444 | 8/1995 | Pruyssers ................................. 602/26 |
| 5,460,599 | 10/1995 | Davis et al. ............................... 602/26 |
| 5,683,353 | 11/1997 | Hamersley ................................ 602/16 |

*Primary Examiner*—Linda C. Dvorak
*Attorney, Agent, or Firm*—Rodney F. Brown

[57] ABSTRACT

A hinge is provided for an orthopedic brace having an adjustable range of rotation. The hinge includes an outer member and an inner member that are rotatably connected in parallel alignment to one another. The peripheral edge of the outer member has a plurality of rotation limiting notches formed therein and the peripheral edge of the inner member has a rotation limiting face formed therein that is selectively alignable with one of the rotation limiting notches. Each of the peripheral edges also has a locking notch formed therein that is selectively alignable with the other. A rotation limiting stop is provided at the peripheral edge of the inner and outer members that is selectively positionable in one of the rotation limiting notches to define an adjustable range of rotation during a rotation mode of hinge operation. Rotation of the inner member is limited when the rotation limiting face engages the rotation limiting stop positioned in the selected notch. Alternatively, the rotation limiting stop is selectively positionable in the locking notches to lock the hinge against rotation in a locked mode of hinge operation. The hinge also includes a stop retainer, which retains the rotation limiting stop in the selected rotation limiting notch or locking notch during a rotation or locking mode of hinge operation, respectively, and which enables repositioning of the rotation limiting stop in an alternately selected rotation limiting notch during an adjustment mode of operation.

23 Claims, 5 Drawing Sheets

HINGE FOR AN ORTHOPEDIC BRACE HAVING A SELECTIVELY POSITIONABLE STOP TO LIMIT ROTATION

This a continuation-in-part application of Ser. No. 08/563,659 filed on Nov. 28, 1995, now U.S. Pat. No. 5,672,152.

TECHNICAL FIELD

The present invention relates generally to orthopedic braces, and more particularly to a hinge for an orthopedic brace, wherein the hinge has a range of rotation that is adjustable by means of a stop selectively positionable in one of a plurality of notches formed in the periphery of the hinge.

BACKGROUND OF THE INVENTION

Hinges for orthopedic braces having an adjustable range of rotation in the extension and flexion direction are well known in the art, for example, as disclosed by U.S. Pat. No. 4,481,941 to Rolfes. The hinge of Rolfes is provided with a pair of threaded screws that function as stops to limit rotation of the hinge. Each screw is selectively threadably securable in one of a plurality of correspondingly threaded holes formed in the body of the hinge. The range of rotation of the hinge is a function of the specific holes selected by the user. Thus, each hole provides the hinge with a different range of rotation when a screw is threadably secured therein. The range of rotation of the hinge is adjusted by unscrewing at least one of the screws from its respective hole and rescrewing the screw into another hole. It has been found, however, that the task of adjusting the range of rotation of the hinge can be difficult because sufficient dexterity is required to maneuver the relatively small screws into and out of the threaded holes and because the screws are susceptible to being misplaced or lost during this task.

An alternate adjustable hinge disclosed by U.S. Ser. No. 401,933 to De Camp, facilitates adjusting the rotational range of the hinge by substituting pins for threaded screws to limit rotation of the hinge. The pins have a smooth surface that enables them to slide into and out of the holes formed in the body of the hinge. The pins are secured in the selected holes of the hinge by means of a leaf spring attached to each pin that biases the pin into its respective hole in a direction parallel to the axis of hinge rotation. Repositioning the pins of De Camp requires less dexterity than repositioning the screws of Rolfes. Nevertheless, adjusting the rotational range of the hinge of De Camp is not entirely without difficulty because a degree of dexterity is still required to pry the leaf spring away from the body of the hinge and remove the pin from the hole. As such, a hinge for an orthopedic brace having an adjustable range of rotation is needed, wherein the hinge is relatively easy to adjust to a desired rotational range in the extension or flexion direction.

Accordingly, it is an object of the present invention to provide a hinge for an orthopedic brace having an adjustable range of rotation in the extension and flexion directions. It is another object of the present invention to provide such a hinge for an orthopedic brace, wherein the hinge has a stop that readily enables adjustment of the rotational range of the hinge by selectively positioning the stop in one of a plurality of rotation limiting positions around the periphery of the hinge. It is still another object of the present invention to provide such a hinge for an orthopedic brace, wherein the stop is resistant to inadvertent slippage from its selected rotation limiting position during rotation of the hinge, yet the stop is readily repositionable to an alternately selected rotation limiting position during adjustment of the rotational range of the hinge. It is a further object of the present invention to provide a hinge for an orthopedic brace, wherein the hinge is lockable to prevent rotation thereof. It is still a further object of the present invention to provide such a hinge for an orthopedic brace, wherein the hinge has a stop that readily enables locking the hinge against rotation by selectively positioning the stop in a locked position at the periphery of the hinge. These objects and others are achieved by the invention described hereafter.

SUMMARY OF THE INVENTION

The present invention is a hinge for an orthopedic brace comprising an outer member and an inner member that are parallelly aligned and rotatably connected by a concentric pivotal connector. The peripheral edge of the outer member has a plurality of rotation limiting notches formed therein and the peripheral edge of the inner member has a rotation limiting face formed therein that is selectively alignable with one of the rotation limiting notches in the outer member by rotation of the inner member relative to the outer member about the pivotal connector. Each of the peripheral edges also has a locking notch formed therein that is selectively alignable with the other by rotation of the outer or inner member about the pivotal connector.

The hinge additionally comprises a rotation adjustment member having a rotation limiting stop. The rotation limiting stop is selectively positionable in one of the rotation limiting notches in the outer member to define an adjustable range of rotation of the inner member about the pivotal connector during a rotation mode of hinge operation. Rotation of the inner member is limited when the rotation limiting face of the inner member engages the rotation limiting stop positioned in a selected notch during rotation of the inner member relative to the outer member. Alternatively, the rotation limiting stop is selectively positionable in the locking notches of the outer and inner members to lock the outer and inner members against rotation about the pivotal connector during a locked mode of hinge operation.

The rotation adjustment member also has a stop retainer that includes a pivot aperture to selectively receive the pivotal connector and anchor the rotation adjustment member to the hinge. In accordance with one embodiment, the pivot aperture has a first widened section, a second widened section and a narrowed section positioned between the first and second widened sections. The first widened section has a width at least as great as the width of the pivotal connector to receive the pivotal connector when the hinge is in the rotation mode of operation. The second widened section likewise has a width at least as great as the width of the pivotal connector to receive the pivotal connector when the hinge is in an adjustment mode of hinge operation. The narrowed section selectively has an unexpanded width or an expanded width. The unexpanded width is narrower than the width of the pivotal connector to retain the pivotal connector in the first widened section when the hinge is in the rotation mode and to retain the pivotal connector in the second widened section when the hinge is in the adjustment mode. The expanded width is substantially equal to the width of the pivotal connector to receive the pivotal connector when the hinge is in a transition mode.

In accordance with an alternate embodiment, the pivot aperture has a single widened section continuously tapering into a narrowed section. The widened section has a width at least as great as the width of the pivotal connector to receive the pivotal connector when the hinge is in the rotation mode of operation. The narrowed section selectively has an unexpanded width or an expanded width. The unexpanded width is narrower than the width of the pivotal connector. The expanded width is substantially equal to the width of the pivotal connector to receive the pivotal connector when the hinge is in the adjustment and transition modes.

In the rotation mode of operation, the hinge is freely rotatable within the adjustable rotation range defined by the rotation limiting stop. As the hinge rotates, however, the rotation adjustment member remains rotatably and radially fixed relative to the outer member, while rotatably displacable relative to the inner member. In the transition mode of operation, the rotation adjustment member is radially displacable, but rotatably fixed relative to the outer member, enabling the hinge to selectively transition between the rotation and adjustment modes. In the adjustment mode of operation, the rotation adjustment member is rotatably displacable, but radially fixed relative to the outer member, enabling selective repositioning of the rotation limiting stop in an alternate rotation limiting notch to adjustably redefine the rotation range of the hinge.

In a preferred embodiment, the hinge is augmented with a second rotation adjustment member that is substantially identical to the above-described first rotation adjustment member. In this embodiment, the rotation limiting stop of the first rotation adjustment member is positionable on the forward arc of the peripheral edge of the outer and inner members to reside in one of the rotation limiting notches formed therein and serve as a rotation limiting stop for a first direction of rotation. The rotation limiting stop for the second rotation adjustment member is opposingly positionable on the rearward arc of the peripheral edge of the outer and inner members to reside in one of the rotation limiting notches formed therein and serve as a rotation limiting stop for the opposite direction of rotation. In the preferred embodiment, the hinge is further provided with a redundant second outer member that is substantially identical to the first outer member described above. The second outer member is parallelly and concentrically alignable with the first outer member to operate in a complimentary manner therewith.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
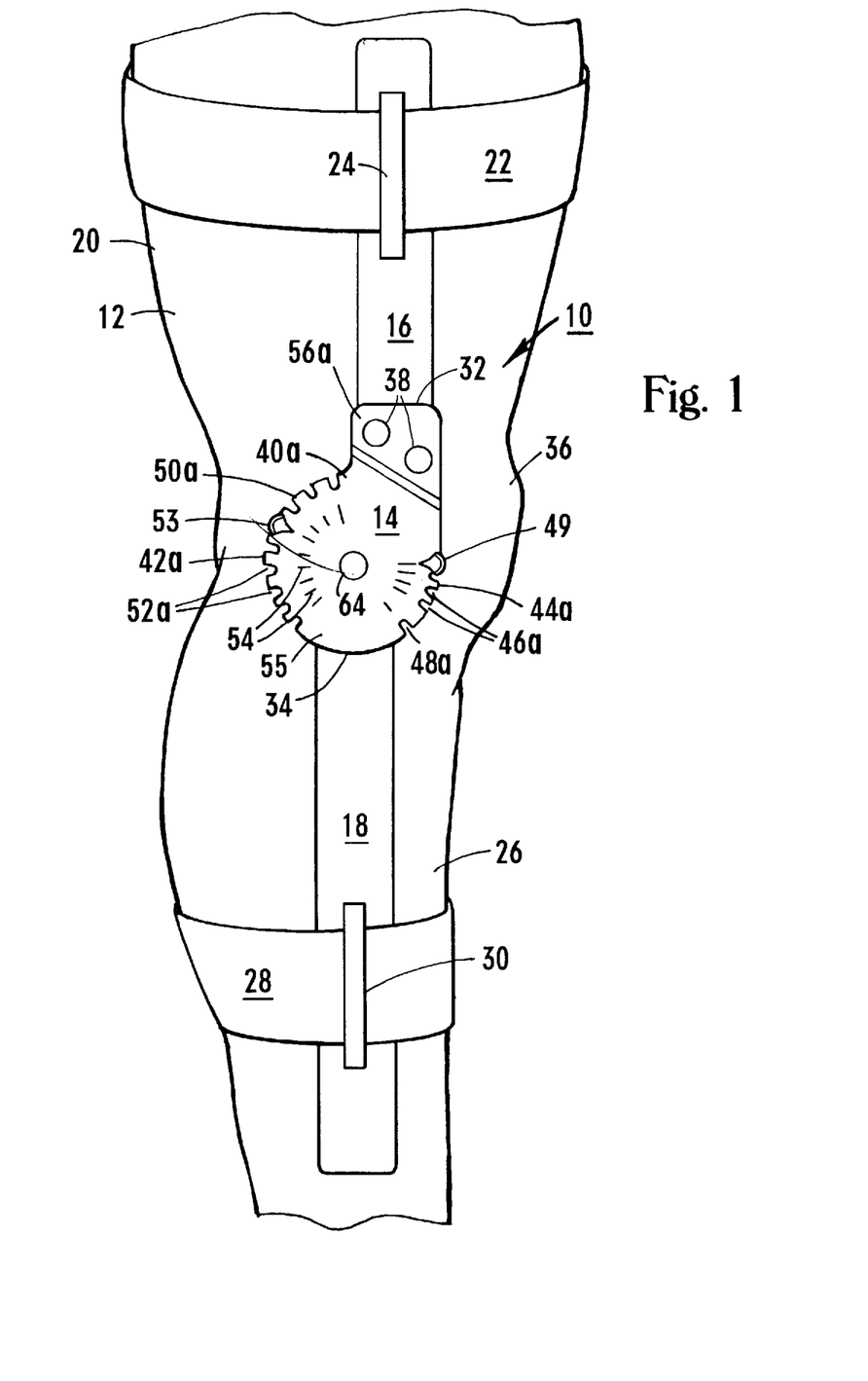
FIG. 1 is a side view of a leg having an orthopedic brace employing the hinge of the present invention mounted thereon.

Referring initially to FIG. 1, a hinged orthopedic brace is shown and generally designated 10. For purposes of illustration, the hinged orthopedic brace 10 shown and described herein is a postoperative knee brace mounted on the right leg 12 of a user, although it is understood that the skilled artisan can readily adapt the instant postoperative knee brace 10 to the opposite leg or to other types of hinged braces for the knee or other joints of the body in accordance with the instant teaching. The brace 10 comprises a novel hinge 14 in combination with conventional components including an upper arm 16 and a lower arm 18. Both the upper and lower arms 16, 18 are substantially rigid, preferably formed from a lightweight, high-strength material, such as aluminum or stainless steel. The upper arm 16 extends substantially the length of the upper leg 20 and is retained in removable engagement therewith by means of an adjustable upper leg strap 22 threaded through an upper strap loop 24 on the upper arm 16. The lower arm 18 extends substantially the length of the lower leg 26 and is similarly retained in removable engagement therewith by means of an adjustable lower leg strap 28 threaded through a lower strap loop 30 on the lower arm 18. Although not shown, additional upper and lower leg straps and strap loops can be provided to further secure the brace 10 to the leg 12. The upper and lower arms 16, 18 have upper and lower proximal ends 32, 34, respectively. The upper proximal end 32 is oriented proximal to the knee joint 36 and is attached to the hinge 14 by conventional fasteners 38, such as fastening rivets shown here. The lower proximal end 34 is integral with the hinge 14 as described hereafter.

The hinge 14 is configured to provide the brace 10 with an adjustable range of extension and flexion rotation during a rotation mode of hinge operation. The terms "anterior" and "posterior" are used hereafter to identify various hinge components. The terms describe the orientation of a given component relative to the hinge 14, rather than relative to the knee joint 36.

Figure 2:
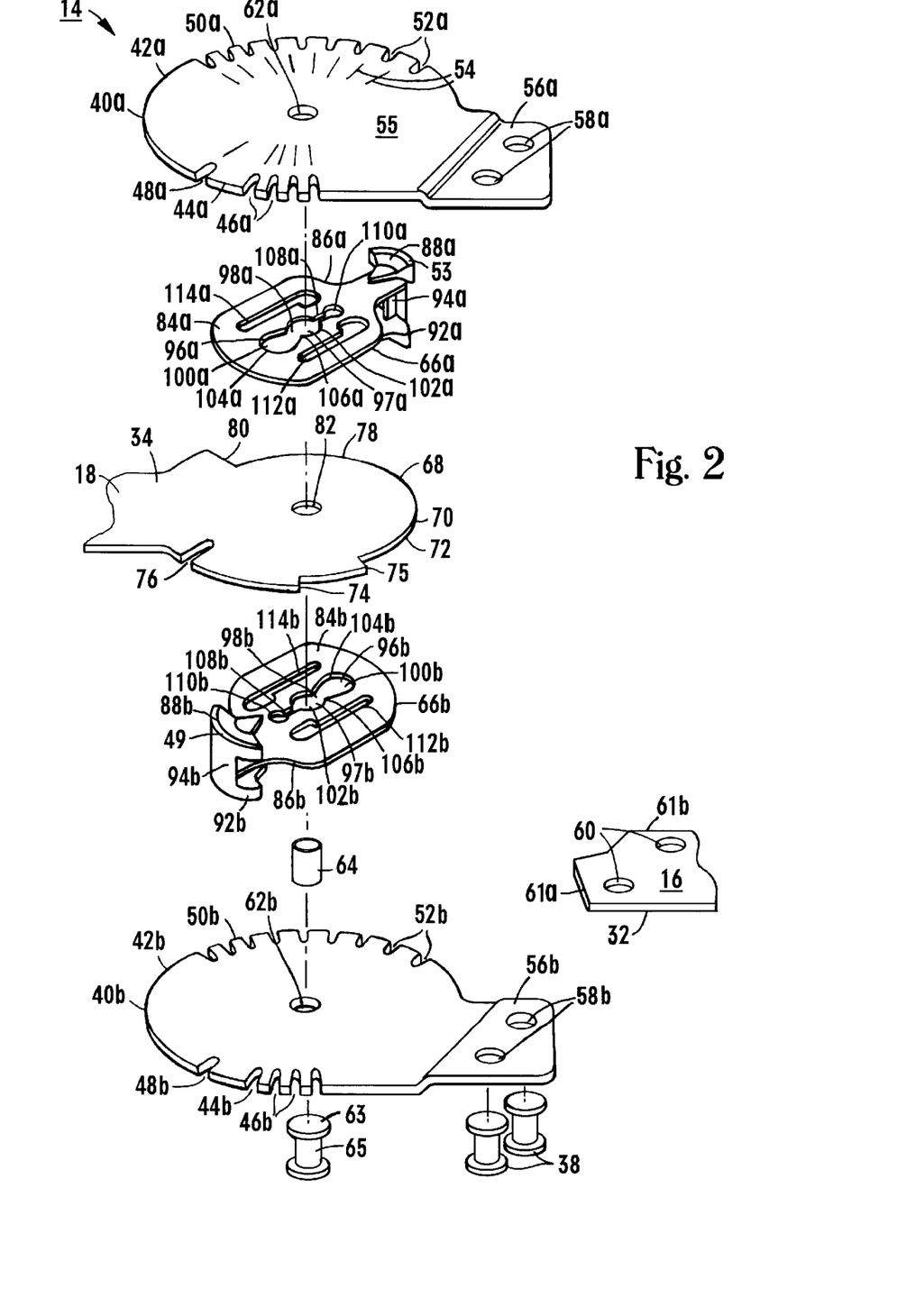
FIG. 2 is an exploded perspective view of the hinge of FIG. 1.

The hinge 14 comprises an anterior outer member 40a adapted to be positioned on the front side of the hinge 14 distal to the knee joint 36. The anterior outer member 40a is formed from a rigid, lightweight, high-strength material, such as aluminum or stainless steel, and has a planar, substantially circular configuration bordered by a peripheral edge 42a defining the circumference of the anterior outer member 40a. The forward arc 44a of the peripheral edge 42a has a plurality of extension limiting notches 46a and a locking notch 48a formed therein that are disposed at circumferentially spaced intervals along the forward arc 44a to receive an extension limiting stop 49 selectively positioned adjacent to the forward arc 44a. The rearward arc 50a of the peripheral edge 42a has a plurality of flexion limiting notches 52a formed therein that are disposed at circumferentially spaced intervals along the rearward arc 50a to receive a flexion limiting stop 53 selectively positioned adjacent to the rearward arc 50a. The notches 46a, 48a, 52a shown herein are U-shaped, but it is understood that substantially any open-ended indentation in the peripheral edge 42a can function as notches 46a, 48a, 52a. A plurality of rotation limit markers 54 are provided on the face 55 of the anterior outer member 40a. The markers 54 are positioned radially inward from the peripheral edge 42a and each marker 54 aligned with a corresponding extension limiting notch 46a, locking notch 48a, or flexion limiting notch 52a, respectively.

The anterior outer member 40a is provided with a fastening extension 56a enabling attachment of the anterior outer member 40a to the proximal end 32 of the upper arm 16 of the brace 10. Referring additionally to FIG. 2 in association with FIG. 1, the fastening extension 56a is shown to have a pair of fastening apertures 58a formed therethrough to receive the fasteners 38. The proximal end 32 of the upper arm 16 likewise has a pair of fastening apertures 60 correspondingly formed therethrough to receive the fasteners 38. The proximal end 32 is also provided with a maximum extension stop 61a and a maximum flexion stop 61b. Although the anterior outer member 40a and upper arm 16 are described herein as distinctly separate elements fastened together by the fasteners 38, it is apparent that the upper arm 16 and anterior outer member 40a can also be integrally formed as a single unitary structure within the scope of the present invention obviating the presence of the fasteners 38.

The anterior outer member 40a is further provided with a pivot aperture 62a formed through the center thereof. The hinge 14 has a pivotal connector which is a member connecting the hinge elements described hereafter and about which the hinge elements pivot. In a preferred embodiment, the pivotal connector comprises a pivoting rivet 63 and a cylindrical bushing 64. The pivoting rivet 63 has a body 65 with an outside diameter substantially equal to the diameter of the pivot aperture 62a. The bushing 64 is rotatably retained around the body 65, having an inside diameter at least substantially equal to the outside diameter of the body 65, but having a length substantially less than that of the body 65. Accordingly, the pivot aperture 62a receives the rivet body 65, but not the bushing 64.

The hinge 14 further comprises a posterior outer member 40b that is substantially identical to the anterior outer member 40a, but is adapted to be positioned on the back side of the hinge 14 proximal to the knee joint 36. Components of the posterior outer member 40b corresponding to like components of the anterior outer member 40a are identified by the same reference number as the components of the anterior outer member 40a, but are distinguished by the suffix "b". Accordingly, the posterior outer member 40b has a peripheral edge 42b with a forward arc 44b, including a plurality of extension limiting notches 46b and a locking notch 48b to receive the extension limiting stop 49, and a rearward arc 50b including a plurality of flexion limiting notches 52b to receive the flexion limiting stop 53. The anterior and posterior outer members 40a, 40b are concentrically positioned in parallel planes on opposite sides of the hinge 14 and are rotationally fixed relative to each other such that the notches 46a, 48a, 52a in the peripheral edge 42a of the anterior outer member 40a are fixably aligned with their counterpart notches 46b, 48b, 52b in the peripheral edge 42b of the posterior outer member 40b. The posterior outer member 40b is provided with a fastening extension 56b and fastening apertures 58b enabling attachment of the posterior outer member 40b to the proximal end 32 of the upper arm 16 of the brace 10 in a like manner as the anterior outer member 40a. Alternatively, the upper arm 16 and posterior outer member 40b can be integrally formed as a single unitary structure. The posterior outer member 40b is provided with a pivot aperture 62b formed through the center thereof in alignment with the pivot aperture 62a of the anterior outer member 40a to similarly receive the rivet body 65, but not the bushing 64.

The hinge 14 additionally comprises a flexion adjustment member 66a, an inner member 68, and an extension adjustment member 66b, which are concentrically positioned in series between the anterior and posterior outer members 40a, 40b. The inner member 68 is formed from a rigid, lightweight, high-strength material, such as aluminum or stainless steel, and has a planar, substantially circular configuration bordered by a peripheral edge 70 defining the circumference of the inner member 68. The forward arc 72 of the peripheral edge 70 has an extension limiting face 74, a maximum extension limiting face 75, and a locking notch 76 formed therein that are disposed at circumferentially spaced intervals along the forward arc 72. The extension limiting face 74 is provided to abut the extension limiting stop 49 and the locking notch 76 is provided to receive the extension limiting stop 49, respectively. The maximum extension limiting face 75 is provided to abut the maximum extension stop 61a, preventing overextension of the hinge 14 when the extension stop 49 is disengaged from the extension limiting notches 46a, 46b in a manner described hereafter. The rearward arc 78 of the peripheral edge 70 has a flexion limiting face 80 formed therein to abut the flexion limiting stop 53 or the maximum flexion stop 61b when the flexion stop 53 is disengaged from the flexion limiting notches 52a, 52b. The inner member 68 is integrally formed as a single unitary structure with the proximal end 34 of the lower arm 18 of the brace 10. Alternatively, the inner member 68 and lower arm 18 are separate elements joined in the manner of the upper arm 16 and the anterior and posterior outer members 40a, 40b. The inner member 68 is provided with a pivot aperture 82 formed through the center thereof in alignment with the pivot apertures 62a, 62b. The diameter of the pivot aperture 82 is at least substantially equal to the outside diameter of the bushing 64 to rotatably receive the rivet body 65 and bushing 64.

Figure 3:
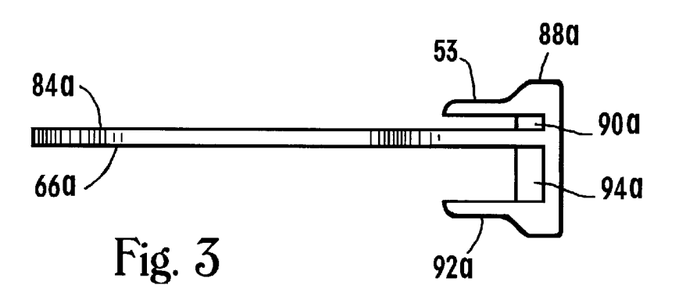
FIG. 3 is a side elevational view of the flexion adjustment member of the hinge of FIG. 1.

Referring additionally to FIG. 3 in association with FIGS. 1 and 2, an embodiment of the flexion adjustment member 66a is shown, formed from a relatively flexible, lightweight, high-strength material, such as a stiffened, yet pliant, plastic, which produces relatively little friction when slidably engaging the anterior outer member 40a and inner member 68. The flexion adjustment member 66a comprises a flexion stop retainer 84a and the flexion limiting stop 53. The flexion stop retainer 84a has a planar configuration. The flexion limiting stop 53 is positioned at the rearward peripheral edge 86a of the flexion stop retainer 84a in a substantially perpendicular orientation with the plane of the flexion stop retainer 84a, such that the flexion limiting stop 53 abuts the rearward arcs 50a, 50b of the anterior and posterior outer members 40a, 40b, respectively. The flexion limiting stop 53 includes an anterior head 88a, an anterior post 90a, a posterior head 92a and a posterior post 94a. The anterior post 90a is configured to conformingly fit within the flexion limiting notches 52a and to fit in abutment with the flexion limiting face 80. The anterior head 88a sits atop the anterior post 90a and is configured to facilitate retention of the anterior post 88a in the notches 52a. The anterior head 88a is tapered in the radial direction of the pivoting rivet 64, thereby forming a pointer that points to the rotation limit marker 54 on the face 55 of the anterior outer member 40a that is aligned with the notch 52a in which the anterior post 88a is retained. The posterior post 94a is similarly configured to conformingly fit within the flexion limiting notches 52b and to fit in abutment with the flexion limiting face 80. The posterior head 92a sits atop the posterior post 94a and is configured similar to the anterior head 88a, facilitating retention of the posterior post 94a in the notches 52b.

The flexion stop retainer 84a is provided with a pivot aperture 96a having a plurality of sections including a first widened section 97a, a narrowed section 98a and a second widened section 100a in selective alignment with the pivot apertures 62a, 62b, 82 to selectively receive the rivet body 65 and bushing 64. The first widened section 97a has a concave arcuate boundary 102a providing the first widened section 97a with a width substantially equal to or greater than the width of the bushing 64 to rotatably receive the rivet body 65 and bushing 64. The second widened section 100a similarly has a concave arcuate boundary 104a providing the second widened section 100a with a width at least substantially equal to the width of the bushing 64 to rotatably receive the rivet body 65 and bushing 64. In contrast, the narrowed section 98a has a convex convergent boundary 106a providing the narrowed section 98a with an unexpanded width substantially less than the width of the bushing 64. The continuous boundaries 102a, 104a, 106a define the configuration of the pivot aperture 96a, resembling a figure-eight.

The flexion stop retainer 84a is further provided with a plurality of expansion cutouts including an expansion slit 108a and expansion openings 110a, 112a, 114a. The expansion slit 108a is axially aligned with the pivot aperture 96a, extending from the first widened section 97a through the boundary 104a to the circular axial expansion opening 110a. The elongated lateral expansion openings 112a, 114a are formed in the flexion stop retainer 84a on opposite sides of the pivot aperture 96a, substantially parallel to the longitudinal axis thereof. The configuration and composition of the flexion stop retainer 84a permit expansion of the unexpanded width of the narrowed section 98a to an expanded width under a moderate manual force, enabling the user to manually displace a structure having a width greater than the unexpanded width of the narrowed section 98a, between the first and second widened sections 97a, 100a.

Figure 4:
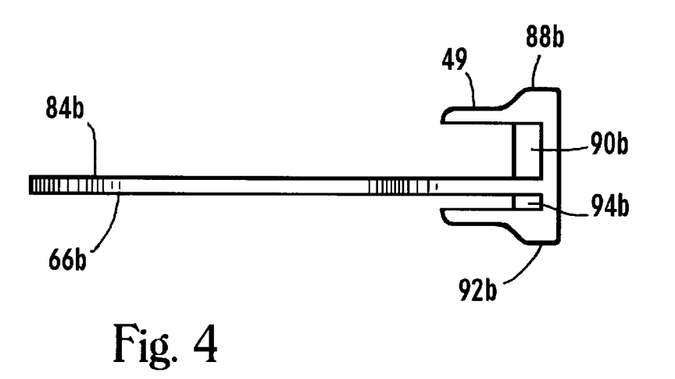
FIG. 4 is a side elevational view of the extension adjustment member of the hinge of FIG. 1.

Referring additionally to FIG. 4 in association with FIGS. 1 and 2, the extension adjustment member 66b is substantially identical to the flexion adjustment member 66a, but is adapted to be positioned on the opposite side of the inner member 68 from the flexion adjustment member 66a. Components of the extension adjustment member 66b corresponding to like components of the flexion adjustment member 66a are identified by the same reference number as the components of the flexion adjustment member 66a, but are distinguished by the suffix "b." Accordingly, the material of the extension adjustment member 66b produces relatively little friction when slidably engaging the posterior outer member 40b and inner member 68. The extension adjustment member 66b comprises an extension stop retainer 84b and the extension limiting stop 49. The extension limiting stop 49 is positioned at the forward peripheral edge 86b of the planarly configured extension stop retainer 84b in a substantially perpendicular orientation, such that the extension limiting stop 49 abuts the forward arcs 44a, 44b of the peripheral edges 42a, 42b of the anterior and posterior outer members 40a, 40b, respectively. The extension limiting stop 49 includes an anterior head 88b, an anterior post 90b, a posterior head 92b and a posterior post 94b. The anterior post 90b fits conformingly within the extension limiting notches 46a and locking notches 48a, 76 and in abutment with the extension limiting face 74. The anterior head 88b sits atop the anterior post 90b, facilitating retention of the anterior post 88b in the notches 46a, 48a, 76. The tapered anterior head 88b points to the rotation limit marker 54 aligned with the notch 46a or 48a in which the anterior post 88b is retained. The posterior post 94b similarly conformingly fits within the extension limiting notches 46b and locking notches 48b, 76 and in abutment with the extension limiting face 74. The posterior head 92b sits atop the posterior post 94b and is configured similar to the anterior head 88b, facilitating retention of the posterior post 94b in the notches 46b, 48b, 76.

The extension stop retainer 84b is provided with a pivot aperture 96b having a first widened section 97b, a narrowed section 98b and a second widened section 100b in selective alignment with the pivot apertures 62a, 62b, 82 to selectively receive the rivet body 65 and bushing 64. The extension stop retainer 84b is further provided with a plurality of expansion cut-outs including an expansion slit 108b, axial expansion opening 110b and lateral expansion openings 112b, 114b. The sections 97b, 98b, 100b, slit 108b, and openings 110b, 112b, 114b are configured and dimensioned substantially identical to the corresponding elements of the flexion stop retainer 84a to function in substantially the same manner as described in greater detail hereafter.

The flexion adjustment member 66a, inner member 68, and extension adjustment member 66b are aligned in parallel planes relative to each other and relative to the anterior and posterior outer members 40a, 40b, such that the flexion adjustment member 66a separates the inner member 68 from the anterior outer member 40a and the extension adjustment member 66b separates the inner member 68 from the posterior outer member 40b. The bushing 64 of the pivotal connector is received by the pivot apertures 82, 96a, 96b, but not by the pivot apertures 62a, 62b, thereby enabling the inner member 68, flexion adjustment member 66a, and extension adjustment member 66b to selectively rotate about the pivotal connector relative to the anterior and posterior outer members 40a, 40b.

The hinge 14 has been described above with the upper arm 16 extending from the anterior outer and posterior outer members 40a, 40b and with the lower arm 18 extending from the inner member 68. It is apparent to the skilled artisan that the hinge 14 can be modified within the scope of the present invention to reverse this configuration, extending the upper arm 16 from the inner member 68 and extending the lower arm 18 from the anterior outer and posterior outer members 40a, 40b. The hinge 14 can correspondingly be modified by reversing the locations of the extension and flexion limiting stops 49, 53 and notches 46a, 46b, 52a, 52b, locating the extension limiting stop 49 and notches 46a, 46b in the rearward arc 50a of the peripheral edge 42a and locating the flexion limiting stop 53 and notches 52a, 52b in the forward arc 44a of the peripheral edge 42a.

It is further noted that the pivotal connector has been disclosed herein as integrally providing means about which the hinge 14 rotates and means for rotatably anchoring the stop retainers 84a, 84b to the hinge 14. It is apparent to the skilled artisan, however, that alternate means are available in accordance with the teaching herein for rotatably anchoring the stop retainers to the hinge 14 independent of the pivotal connector and that such alternate means fall within the scope of the present invention. For example, a pair of off-center posts 116b, 118b, shown in phantom in FIG. 2, can be provided to function as anchors for the stop retainers 84a, 84b. The posts 116b, 118b extend perpendicularly from the posterior outer member 40b to receive the pivot apertures 96a, 96b, respectively. The dimensions of the flexion and extension adjustment members 66a, 66b are also adapted accordingly. A corresponding pair of posts (not shown) are also extended from the anterior outer member 40a.

METHOD OF OPERATION

Figure 5A:
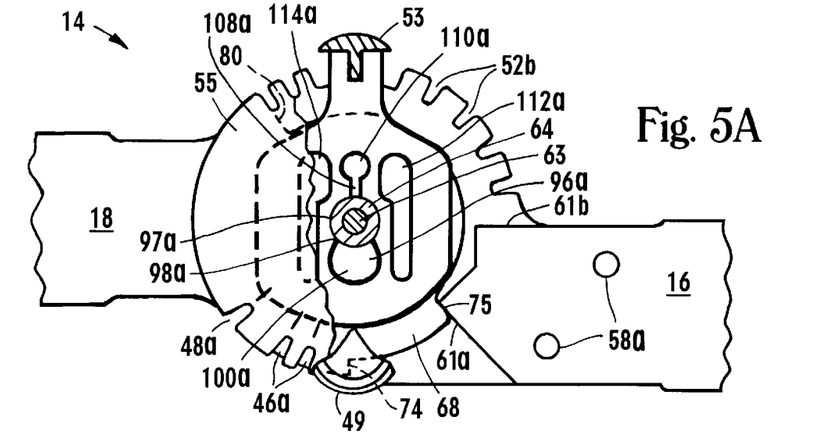
FIG. 5A is a partial cutaway frontal view of the hinge of FIG. 1 in a rotation mode of operation.

The modes of hinge operation are described hereafter with reference to FIGS. 5A, 5B, 5C, 6A, 6B, 6C, 6D and 7. Referring initially to FIG. 5A, the hinge 14 is shown in a rotation mode of operation, wherein the pivotal connector, including the pivoting rivet 63 and bushing 64, is rotatably positioned in the first widened section 97a of the pivot aperture 96a of the flexion stop retainer 84a. The narrow unexpanded width of the narrowed section 98a maintains the position of the pivotal connector in the first widened section 97a preventing inadvertent repositioning of the pivotal connector in the narrowed or second widened sections 98a, 100a during the rotation mode of operation. Although not shown in FIG. 5A, it is apparent that the pivotal connector is simultaneously positioned in the corresponding first widened section 97b of the pivot aperture 96b in the extension stop retainer 84b during the rotation mode of operation. The rotation mode allows rotational operation of the hinge 14 as described below.

Figure 5B:
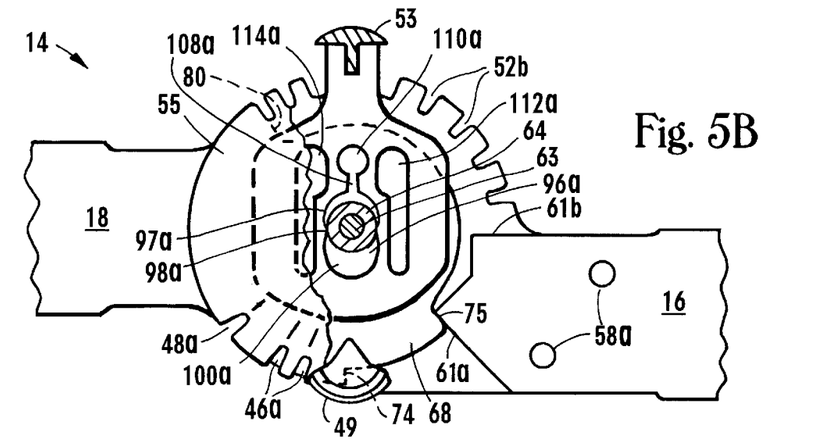
FIG. 5B is a partial cutaway frontal view of the hinge of FIG. 1 in a transition mode of operation.

Referring to FIG. 5B, the hinge 14 is shown in a transition mode of operation, wherein the pivotal connector is positioned in the narrowed section 98a of the pivot aperture 96a by applying a radially outward directed manual force to the flexion stop retainer 84a when the hinge 14 is in the rotation mode of operation. The expansion slit 108a, axial expansion opening 110a, and lateral expansion openings 112a, 114a enable expansion of the width of the narrowed section 98a to an expanded width, which allows the narrowed section 98a to receive the pivotal connector. Although not shown in FIG. 5B, it is apparent that the transition mode of operation is also applicable to the extension stop retainer 84b. The transition mode allows the hinge 14 to transition from the rotation mode to the adjustment mode of operation. It is also apparent that the transition mode allows the hinge 14 to transition from the adjustment mode to the rotation mode of operation by applying a radially inward directed manual force to the flexion stop retainer 84a when the hinge 14 is in the adjustment mode of operation as described below.

Figure 5C:
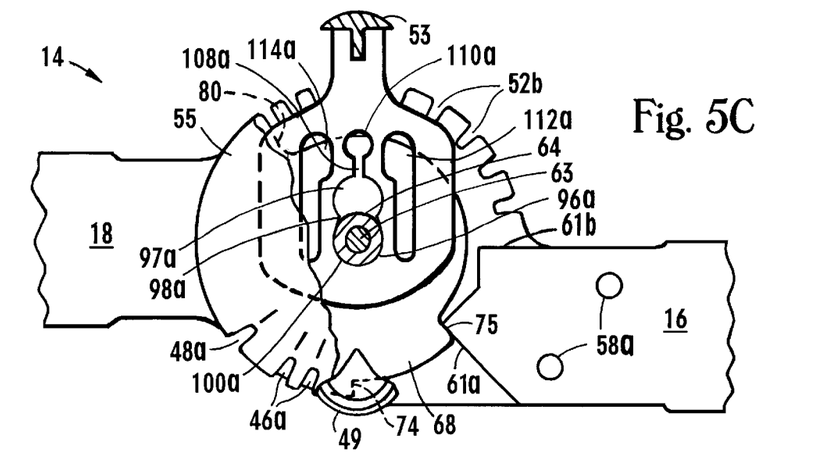
FIG. 5C is a partial cutaway frontal view of the hinge of FIG. 1 in an adjustment mode of operation.

Referring to FIG. 5C, the hinge 14 is shown in an adjustment mode of operation, wherein the pivotal connector is rotatably positioned in the second widened section 100a of the pivot aperture 96a. The narrow unexpanded width of the narrowed section 98a maintains the position of the pivotal connector in the radially inner section 97a, preventing inadvertent repositioning of the pivotal connector in the narrowed or first widened sections 98a, 97a during the adjustment mode of operation. Although not shown in FIG. 5C, it is apparent that the pivotal connector is simultaneously positioned in the corresponding second widened section 100b of the pivot aperture 96b in the extension stop retainer 84b during the adjustment mode of operation. The adjustment mode allows adjustable operation of the hinge 14 as described below.

Figure 6A:
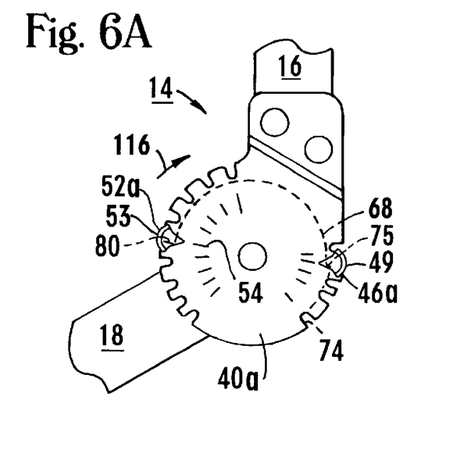
FIG. 6A is a frontal view of the hinge of FIG. 1 in a rotation mode of operation, wherein the hinge is rotated in a first direction to a preselected flexion limit.

Referring to FIG. 6A, rotational operation of the hinge 14 is shown, wherein the lower arm 18 of the brace is rotated about the hinge 14 in a first clockwise direction of rotation indicated by the arrow 116 until the hinge 14 reaches a flexion limit of 60° that has been preselected from a number of flexion limits including 10°, 20°, 30°, 45°, 60°, 75°, 90°, 105°, and 120°. The flexion limit is preselected by positioning the flexion limiting stop 53 in the flexion limiting notch 52a of the anterior outer member 40a corresponding to 60° as indicated by the rotation limit marker 54 adjacent to the flexion limiting notch 52a. The flexion limiting stop 53 is retained in the flexion limiting notch 52a by the flexion stop retainer 84a as described above and shown in FIG. 5A. Thus, when the hinge 14 is rotated in the rotation mode of operation, the flexion limiting stop 53 remains radially and rotatably fixed relative to the anterior outer member 40a, while rotatably displacable relative to the inner member 68. At the flexion limit, the flexion limiting face 80 of the inner member 68 shown in phantom beneath the anterior outer member 40a abuts the flexion limiting stop 53 preventing further rotation of the hinge 14 in the direction of the arrow 116, thereby limiting flexion of the knee joint. Although not shown in FIG. 6A, it is apparent that, at the preselected flexion limit, the flexion limiting stop 53 is simultaneously positioned in the corresponding flexion limiting notch 52b of the posterior outer member 40b.

Figure 6B:
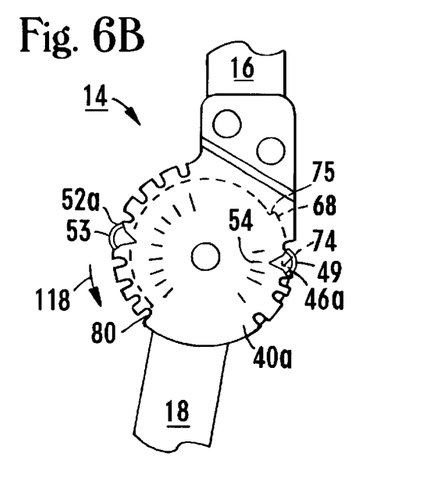
FIG. 6B is a frontal view of the hinge of FIG. 1 in a rotation mode of operation, wherein the hinge is rotated in a second direction to a preselected extension limit.

Referring to FIG. 6B, rotational operation of the hinge 14 is shown, wherein the lower arm 18 of the brace is rotated about the hinge 14 in a second counterclockwise direction of rotation indicated by the arrow 118 until the hinge 14 reaches an extension limit of 10° that has been preselected from a number of extension limits including 0°, 10°, 20°, and 30°. In a manner similar to that described above with respect to the flexion limit, the extension limit is preselected by positioning the extension limiting stop 49 in the extension limiting notch 46a of the anterior outer member 40a corresponding to 10° as indicated by the rotation limit marker 54 adjacent to the extension limiting notch 46a. The extension limiting stop 49 is retained in the extension limiting notch 46a by the extension stop retainer 84b as described above and shown in FIG. 5A. At the extension limit, the extension limiting face 74a of the anterior inner member 66a abuts the extension limiting stop 49 preventing further rotation of the hinge 14 in the direction of the arrow 118, thereby limiting extension of the knee joint. Although not shown in FIG. 6B, it is apparent that, at the preselected extension limit, the extension limiting stop 49 is also positioned in the corresponding extension limiting notch 46b of the posterior outer member 40b.

Figure 6C:
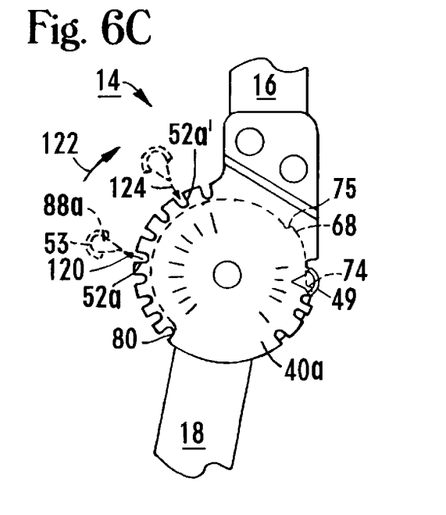
FIG. 6C is a frontal view of the hinge of FIG. 1 in an adjustment mode of operation, wherein the flexion limit of the hinge is adjusted from that of FIG. 6A.

Referring to FIG. 6C, transitional and adjustable operation of the hinge 14 is shown, wherein the flexion limit is adjusted by repositioning the flexion limiting stop 53 from the flexion limiting notch 52a of the anterior outer member 40a corresponding to 60° to the flexion limiting notch 52a' corresponding to 105°. The flexion limiting stop 53 is repositioned by manually grasping the anterior and posterior heads 90b, 92b of the flexion limiting stop 53 and displacing the flexion limiting stop 53 radially outward away from the anterior outer member 40a in the direction of the arrow 120. The pivotal connector expands the boundary of the radially intermediate section 98a, enabling the radially intermediate section 98a to receive the pivotal connector in accordance with the transition mode of operation shown in FIG. 5B. Displacement of the flexion limiting stop 53 is continued until the flexion limiting stop 53 clears the flexion limiting notch 52a, as shown in phantom. The flexion limiting stop 53 is then circumferentially rotated in association with the flexion stop retainer 84b along the peripheral edge 42a of the anterior outer member 40a in the direction of the arrow 122 in accordance with the adjustment mode of operation shown in FIG. 5C. Thus, when the flexion limiting stop 53 is rotated in the adjustment mode of operation, the flexion limiting stop 53 rotates relative to the anterior outer member 40*a*. It is noted that the maximum extension limiting face 75, in cooperation with the maximum extension stop 61*a*, prevents inadvertent overextension of the hinge 14 beyond 0° while in the adjustment mode of operation. The flexion limiting face 80, in cooperation with the maximum flexion stop 61*b*, prevents inadvertent overflexion of the hinge 14 beyond about 130° while in the adjustment mode of operation.

When the anterior head 90*b* of the flexion limiting stop 53 is radially adjacent to the flexion limiting notch 52*a'*, the flexion adjustment member 66*b* is displaced radially inward until the flexion limiting stop 53 is received by the flexion limiting notch 52*a'* in accordance with the transition mode of operation. Although not shown in FIG. 6C, it is apparent that, at the adjusted flexion limit, the flexion limiting stop 53 is simultaneously positioned in the corresponding flexion limiting notch 52*b'* of the posterior outer member 40*b*. Adjustment of the extension limit is also performed in accordance with the present transition and adjustment modes of operation as is readily apparent to the skilled artisan. Upon completion of the transition and adjustment modes of operation, rotational operation of the hinge 14 is resumed with the hinge 14 having an adjusted flexion or extension limit.

Figure 6D:
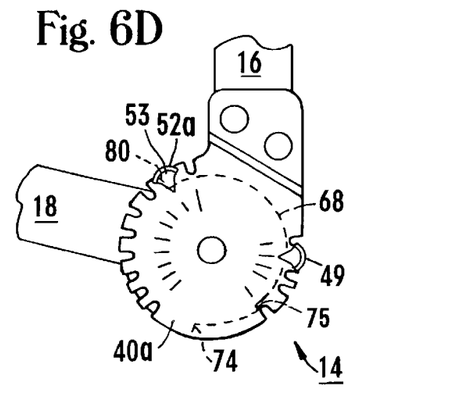
FIG. 6D is a frontal view of the hinge of FIG. 1 in a rotation mode of operation, wherein the hinge is rotated in the first direction to the adjusted flexion limit of FIG. 6C.

Referring to FIG. 6D, rotational operation of the hinge 14 is shown, wherein the lower arm 18 of the brace is rotated about the hinge 14 until the hinge 14 reaches the adjusted flexion limit selected in accordance FIG. 6C. Operation of the hinge 14 with the adjusted flexion limit is substantially the same as described above with respect to FIG. 6A.

Figure 7:
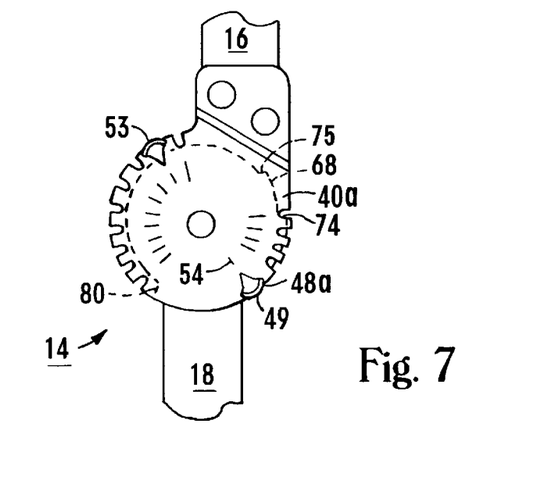
FIG. 7 is frontal view of the hinge of FIG. 1 in a locked mode of operation, wherein the hinge is locked against rotation.

Referring to FIG. 7, the hinge 14 is shown in a locked mode of operation, wherein the hinge 14 is locked at an extension angle of 0° against rotation in either direction. The locked mode is achieved by employing the transition and adjustment modes of operation to position the extension limiting stop 49 in the locking notch 48*a* of the anterior outer member 40*a* as indicated by the rotation limit marker 54 adjacent thereto. The extension limiting stop 49 is retained in the locking notch 48*a* by the extension stop retainer 84*b*. With the extension limiting stop 49 positioned in this manner, rotation of the hinge 14 in either direction is blocked. Although not shown in FIG. 7, it is apparent that, in the locked mode of operation, the extension limiting stop 49 is also simultaneously positioned in the corresponding locking notches 46*b* and 76 of the posterior outer member 40*b* and the inner member 68, respectively. It is further apparent to the skilled artisan that the hinge 14 can be modified by relocating the locking notches 48*a*, 48*b*, 76 to other locations on the forward arcs 44*a*, 72 or to locations on the rearward arcs 50*a*, 78, enabling a locked mode of hinge operation at other fixed angles of flexion or extension.

Figure 8:
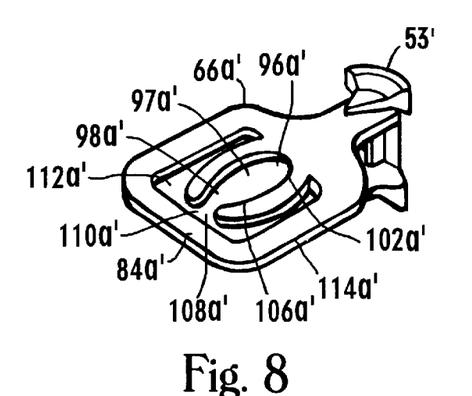
FIG. 8 is a perspective view of an alternate embodiment of a rotation adjustment member having utility in the hinge of the present invention.

Referring to FIG. 8, an alternate embodiment of a flexion adjustment member 66*a'* is shown. Components of the flexion adjustment member 66*a'* corresponding to like components of the flexion adjustment member 66*a* are identified by the same reference character as the components of the flexion adjustment member 66*a*, but are distinguished by the addition of a prime after the reference character. The flexion adjustment member 66*a'* is formed from substantially the same material as the flexion adjustment member 66*a* and is positioned in substantially the same manner relative to the inner member 68 and the anterior and posterior outer members 40*a*, 40*b*. The flexion adjustment member 66*a'* comprises a flexion stop retainer 84*a'* and a flexion limiting stop 53'. The flexion stop retainer 84*a'* has a planar configuration in the manner of the flexion adjustment member 66*a* and the flexion limiting stop 53' is substantially identical to the flexion limiting stop 53 of the flexion adjustment member 66*a*.

The flexion stop retainer 84*a'* is provided with a pivot aperture 96*a'* having a single widened section 97*a'* continuously tapering into a narrowed section 98*a'* in selective alignment with the pivot apertures 62*a*, 62*b*, 82 to selectively receive the rivet body 65 and bushing 64. The widened section 97*a'* has a concave arcuate boundary 102*a'* providing the widened section 97*a'* with a width substantially equal to or greater than the width of the bushing 64 to rotatably receive the rivet body 65 and bushing 64. In contrast, the narrowed section 98*a'* has a continuously convergent boundary 106*a'* providing the narrowed section 98*a'* with an unexpanded width substantially less than the width of the bushing 64. The continuous boundaries 102*a'*, 106*a'* define the configuration of the pivot aperture 96*a'* resembling a tear drop.

The flexion stop retainer 84*a'* is further provided with a plurality of continuous expansion cut-outs including an expansion slit 108*a'* and expansion openings 110*a'*, 112*a'*, 114*a'*. The expansion slit 108*a'* is axially aligned with the pivot aperture 96*a'*, extending from the widened section 97*a'* through the boundary 106*a'* to the axial expansion opening 110*a'*. The elongated lateral expansion openings 112*a'*, 114*a'* are formed in the flexion stop retainer 84*a'* on opposite sides of the pivot aperture 96*a'*, substantially parallel to the longitudinal axis thereof. The configuration and composition of the flexion stop retainer 84*a'* permit expansion of the unexpanded width of the narrowed section 98*a'* to one or more expanded widths under a moderate manual force, enabling the user to manually displace a structure having a width greater than the unexpanded width of the narrowed section 98*a'* away from the widened section 97*a'* into the narrowed section 98*a'*.

Although not shown, a corresponding extension adjustment member is also provided in accordance with the present embodiment. The extension adjustment member is substantially identical to the flexion adjustment member 66*a'*, but is adapted to be positioned on the opposite side of the inner member 68 from the flexion adjustment member 66*a'*.

Operation of a hinge employing the flexion adjustment member 66*a'* and a corresponding extension adjustment member is substantially similar to that described above with respect to the hinge 14 employing the flexion and extension adjustment members 66*a*, 66*b*. During the rotation mode of operation, the pivotal connector is rotatably positioned in the widened section 97*a'* of the pivot aperture 96*a'*. The narrow unexpanded width of the narrowed section 98*a'* acts as a spring to bias and maintain the position of the pivotal connector in the widened section 97*a'* preventing inadvertent repositioning of the pivotal connector in the narrowed section 98*a'*. The pivotal connector is simultaneously positioned in the same manner in the corresponding extension adjustment member. The rotation mode allows rotational operation of the hinge employing the flexion adjustment member 66*a'* and the corresponding extension adjustment member in substantially the same manner as described above with reference to the hinge 14.

During the transition mode of operation, the pivotal connector is positioned in a portion of the narrowed section 98*a'* of the pivot aperture 96*a'* proximal to the widened section 97*b'* by applying a radially outward directed manual force to the flexion stop retainer 84a' while the hinge is in the rotation mode. The expansion slit 108a', axial expansion opening 110a', and lateral expansion openings 112a', 114a' enable expansion of the width of the narrowed section 98a' to a first expanded width, which allows the proximal portion of the narrowed section 98a' to receive the pivotal connector. The pivotal connector is simultaneously positioned in the same manner in the corresponding extension adjustment member. The transition mode allows the hinge to transition from the rotation mode to the adjustment mode by application of a manual force in substantially the same manner as described above with reference to the hinge 14 and allows the hinge to transition from the adjustment mode to the rotation mode by means of a radially inward directed spring biasing force applied by the narrowed section 98a' to the pivotal connector.

During the adjustment mode of operation, the pivotal connector is rotatably positioned in a portion of the narrowed section 98a' of the pivot aperture 96a' distal to the widened section 97b' by continuing to apply a radially outward directed manual force to the flexion stop retainer 84a' while the hinge is in the transition mode of operation. The expansion slit 108a', axial expansion opening 110a', and lateral expansion openings 112a', 114a' enable continued expansion of the width of the narrowed section 98a' to a second expanded width greater than or equal to the first expanded width, which allows the distal portion of the narrowed section 98a' to receive the pivotal connector. The pivotal connector is simultaneously positioned in the same manner in the corresponding extension adjustment member. Throughout the adjustment mode of operation, the narrowed section 98a' continues to apply a radially inward directed spring biasing force to the pivotal connector, enabling the hinge to return to the rotation mode of operation upon withdrawal of the radially outward directed manual force.

While the particular hinges for an orthopedic brace having an adjustable range of rotation as herein shown and disclosed in detail are fully capable of obtaining the objects and providing the advantages hereinbefore stated, it is to be understood that the hinges are merely illustrative of presently preferred embodiments of the invention and that other embodiments are possible within the scope of the present invention.

We claim:

1. A hinge for an orthopedic brace comprising:
   a first member having a first peripheral edge;
   a second member having a second peripheral edge;
   a pivotal connector connecting said first and second members;
   a notch formed in said first peripheral edge;
   a limiting face formed in said second member;
   a stop selectively positionable in said notch and engageable with said limiting face upon rotation of said second member relative to said first member; and
   a stop retainer having an aperture receiving said pivotal connector, wherein said aperture includes a widened section and a narrowed section adjacent to said widened section, said narrowed section selectively having an unexpanded width or an expanded width.

2. A hinge as recited in claim 1 having a rotation mode of operation, wherein said widened section receives said pivotal connector and said narrowed section has said unexpanded width.

3. A hinge as recited in claim 1 having a transition mode of operation, wherein said narrowed section has said expanded width and receives said pivotal connector.

4. A hinge as recited in claim 3 having an adjustment mode of operation, wherein said expanded width is a first expanded width proximal to said widened section and said narrowed section has a second expanded width distal to said widened section greater than or equal to said first expanded width.

5. A hinge as recited in claim 1, wherein said widened section is a first widened section and said aperture further includes a second widened section with said narrowed section positioned between said first and second widened sections, said unexpanded width of said narrowed section being narrower than said first or second widened sections.

6. A hinge as recited in claim 5 having an adjustment mode of operation, wherein said second widened section receives said pivotal connector and said narrowed section has said unexpanded width.

7. A hinge as recited in claim 5, wherein said second widened section has a width substantially equal to or greater than the width of said pivotal connector.

8. A hinge as recited in claim 1, wherein said widened section has a width substantially equal to or greater than the width of said pivotal connector.

9. A hinge as recited in claim 1, wherein said unexpanded width of said narrowed section is substantially less than the width of said pivotal connector.

10. A hinge as recited in claim 1, wherein said expanded width of said narrowed section is substantially equal to the width of said pivotal connector, said narrowed section having said expanded width in response to an expansion force applied to said stop retainer.

11. A hinge as recited in claim 1, wherein stop retainer includes one or more expansion cut-outs.

12. A hinge as recited in claim 1, wherein said notch is a first notch and said hinge further comprises a second notch formed in said first peripheral edge at a spaced interval from said first notch, said stop selectively positionable in said first notch and engageable with said limiting face, thereby defining a first range of rotation of said hinge, and said stop selectively positionable in said second notch and engageable with said limiting face, thereby defining a second range of rotation of said hinge.

13. A hinge as recited in claim 12, wherein said stop is an extension limiting stop, said limiting face is an extension limiting face, and said first and second notches are a set of extension limiting notches formed in a first side of said first peripheral edge, and said hinge further comprises a flexion limiting face formed in said second peripheral edge and a set of flexion limiting notches including a first flexion limiting notch and a second flexion limiting notch formed in a second side of said first peripheral edge opposite said first side.

14. A hinge as recited in claim 13, wherein said extension limiting stop positioned in said first extension limiting notch defines an extension limit of said first range of rotation and said extension limiting stop positioned in said second extension limiting notch defines an extension limit of said second range of rotation, and said hinge further comprises a flexion limiting stop selectively positionable in said first or said second flexion limiting notch and engageable with said flexion limiting face upon rotation of said second member relative to said first member, wherein said flexion limiting stop positioned in said first flexion limiting notch defines a flexion limit of said first range of rotation and said flexion limiting stop positioned in said second flexion limiting notch defines a flexion limit of said second range of rotation.

15. A hinge for an orthopedic brace comprising:
   a first member having a first peripheral edge;
   a second member having a second peripheral edge;

a pivotal connector connecting said first and second members;

a notch formed in said first peripheral edge;

a limiting face formed in said second member;

a stop selectively positionable in said notch and engageable with said limiting face upon rotation of said second member relative to said first member;

means for enabling rotation of said hinge while maintaining said stop substantially rotatably fixed relative to said first member during a rotation mode of hinge operation;

means for maintaining said stop in said notch during said rotation mode of hinge operation; and means for enabling rotation of said stop relative to said first member during an adjustment mode of hinge operation.

16. A hinge as recited in claim 15 further comprising means for transitioning between said rotation mode and said adjustment mode of hinge operation.

17. A hinge as recited in claim 16, wherein said transition means is a narrow section of an aperture in a stop retainer anchored to said hinge, said narrow section having an expanded width.

18. A hinge as recited in claim 16, wherein said stop maintaining means is a narrowed section of an aperture in a stop retainer anchored to said hinge, said narrowed section having an unexpanded width.

19. A hinge as recited in claim 15, wherein said hinge rotation enabling means is a widened section of an aperture in a stop retainer anchored to said hinge.

20. A hinge as recite in claim 19, wherein said hinge rotation enabling means is a widened section of an aperture in a stop retain anchored to said hinge.

21. A hinge as recited in claim 15, wherein said stop maintaining means is a narrow section of an aperture in a stop retainer anchored to said hinge, said narrow section having an unexpanded width.

22. A hinge for an orthopedic brace comprising:

a first member having a first peripheral edge;

a second member having a second peripheral edge;

a pivotal connector connecting said first and second members;

a first notch and a second notch formed in said first peripheral edge at a spaced apart interval;

a limiting face formed in said second member;

a rotation adjustment member having a stop retainer and a stop mounted to said stop retainer, wherein said stop is selectively positionable in said notch and engageable with said limiting face upon rotation of said second member relative to said first member and wherein said stop retainer has an aperture including a first widened section to receive said pivotal connector when said hinge is in a rotation mode, a second widened section to receive said pivotal connector when said hinge is in an adjustment mode and a narrowed section having an unexpanded width narrower than the width of said pivotal connector to retain said pivotal connector in said first widened section when said hinge is in said rotation mode and to retain said pivotal connector in said second widened section when said hinge is in said adjustment mode and having an expanded width substantially equal to the width of said pivotal connector to receive said pivotal connector when said hinge is in a transition mode.

23. A hinge for an orthopedic brace comprising:

a first member having a first peripheral edge;

a second member having a second peripheral edge;

a pivotal connector connecting said first and second members;

a first notch and a second notch formed in said first peripheral edge at a spaced apart interval;

a limiting face formed in said second member;

a rotation adjustment member having a stop retainer and a stop mounted to said stop retainer, wherein said stop is selectively positionable in said notch and engageable with said limiting face upon rotation of said second member relative to said first member and wherein said stop retainer has an aperture including a widened section to receive said pivotal connector when said hinge is in a rotation mode and a narrowed section having an unexpanded width narrower than the width of said pivotal connector to retain said pivotal connector in said widened section when said hinge is in said rotation mode and having an expanded width substantially equal to the width of said pivotal connector to receive said pivotal connector when said hinge is in a transition mode or an adjustment mode.

\* \* \* \* \*